(12) United States Patent
Taylor et al.

(10) Patent No.: US 6,652,569 B1
(45) Date of Patent: *Nov. 25, 2003

(54) STENT PLACEMENT AND REMOVAL

(75) Inventors: William N. Taylor, Vancouver (CA); Ian McDougall, North Vancouver (CA)

(73) Assignee: BIU Biomedical Innovations (Urology) Inc. (CA)

( * ) Notice: Subject to any disclaimer, the term of this patent is extended or adjusted under 35 U.S.C. 154(b) by 409 days.

This patent is subject to a terminal disclaimer.

(21) Appl. No.: 09/618,960

(22) Filed: Jul. 19, 2000

Related U.S. Application Data

(63) Continuation-in-part of application No. 09/074,991, filed on May 8, 1998, now Pat. No. 6,258,098.

(51) Int. Cl.⁷ .................................................. A61F 2/06
(52) U.S. Cl. ....................... 623/1.11; 606/108; 623/902
(58) Field of Search ................................ 606/108, 151, 606/191–200, 159; 623/1.1–1.12, 902, 909, 11.11

(56) References Cited

U.S. PATENT DOCUMENTS

| | | |
|---|---|---|
| 3,908,646 A | 9/1975 | Ansari |
| 4,212,304 A | 7/1980 | Finney |
| 4,657,020 A | 4/1987 | Lifton |
| 4,671,795 A | 6/1987 | Mulchin |
| 4,727,866 A | 3/1988 | Livesay et al. |
| 4,790,809 A | 12/1988 | Kuntz |
| 4,820,262 A * | 4/1989 | Finney ........................ 604/8 |
| 4,865,030 A | 9/1989 | Polyak |
| 4,913,683 A | 4/1990 | Gregory |
| 4,963,129 A | 10/1990 | Rusch |
| 4,973,301 A | 11/1990 | Nissenkorn |
| 4,989,299 A * | 2/1991 | Morita ........................ 24/303 |
| 4,997,435 A | 3/1991 | Demeter |
| 5,057,114 A | 10/1991 | Wittich |
| 5,100,423 A | 3/1992 | Fearnot |
| 5,116,309 A | 5/1992 | Coll |
| 5,123,914 A | 6/1992 | Cope |
| 5,176,625 A * | 1/1993 | Brisson ........................ 604/8 |
| 5,312,416 A | 5/1994 | Spaeth |
| 5,322,501 A | 6/1994 | Mahmud-Durrani |
| 5,324,284 A | 6/1994 | Inran |

(List continued on next page.)

FOREIGN PATENT DOCUMENTS

| | | |
|---|---|---|
| EP | 0 276 104 A2 | 7/1988 |
| FR | 2 577 809 | 4/1986 |

OTHER PUBLICATIONS

International Search Report in PCT application No. PCT/CA99/00405; Aug. 23, 1999, 4 pages.

Macaluso, Jr. et al; The Use of the Magnetic Double–J Uretera Stent In Urological Practice; The Journal of Urology; vol. 142; Sep. 1989; pp 701–703.

Dah_Shyong Yu, et al; Nail–Headed Catheter Retriever: A Simple Way to Remove Catheters From Female Patients; Journal of Urology; vol. 154; Jul. 1995; pp 167–168.

Alverez–Vijande; Removal of Ureteric Stents in Women without Cystoscope; British Journal of Urology; vol. 72; pp 388–389.

Siegel, et al; Simplified Method of Indwelling Ureteral Stent Removal; Urology; Nov. 1986; p 429.

Murray K.; Ureteric Stent Retrieval—"A Better Mousetrap" British Jornal of Urology; circa 1990; pp 127–128.

*Primary Examiner*—Glenn K. Dawson
(74) *Attorney, Agent, or Firm*—Ipsolon LLP

(57) ABSTRACT

Placement and non-surgical removal of a ureteral stent is accomplished by suspending a ferromagnetic bead from an indwelling stent. The bead is suspended by a flaccid tether that reduces the likelihood of patient irritation when a shortened stent is used. The bead, tether, and stent assembly are advanced into the patient as a unit via a conventional cystoscope. A magnet-tipped catheter is employed to engage the bead in the bladder and permit removal of the connected stent as the catheter is withdrawn.

13 Claims, 4 Drawing Sheets

U.S. PATENT DOCUMENTS

| | | |
|---|---|---|
| 5,364,340 A | 11/1994 | Coll |
| 5,380,270 A | 1/1995 | Ahmadzadeh |
| 5,387,219 A | 2/1995 | Rappe |
| 5,453,090 A | 9/1995 | Martinez |
| 5,514,178 A | 5/1996 | Torchio |
| 5,593,412 A | 1/1997 | Martinez |
| 5,599,291 A | 2/1997 | Balbierz |
| 5,609,605 A | 3/1997 | Marshall |
| 5,647,843 A | 7/1997 | Mesrobian |
| 5,667,523 A | 9/1997 | Bynon |
| 5,755,781 A | 5/1998 | Jayaraman |
| 5,766,203 A | 6/1998 | Imran |
| 5,782,906 A | 7/1998 | Marshall |
| 5,792,145 A | 8/1998 | Bates |
| 5,817,104 A | 10/1998 | Bilitz |
| 5,824,042 A | 10/1998 | Lombardi |
| 5,824,058 A | 10/1998 | Ravenscroft |
| 5,833,694 A | 11/1998 | Poncet |
| 5,885,258 A | 3/1999 | Sachdeva |
| 6,258,098 B1 * | 7/2001 | Taylor et al. ............... 606/108 |

* cited by examiner

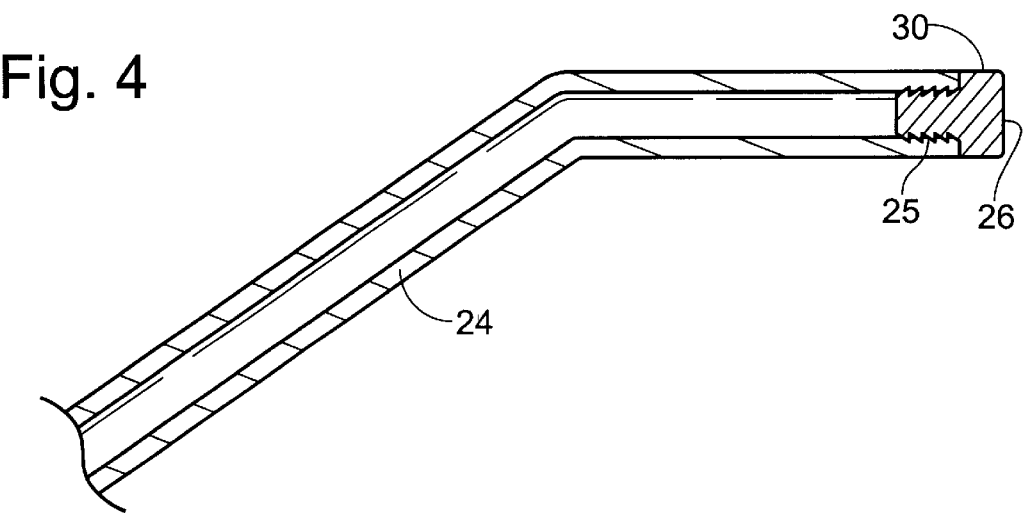
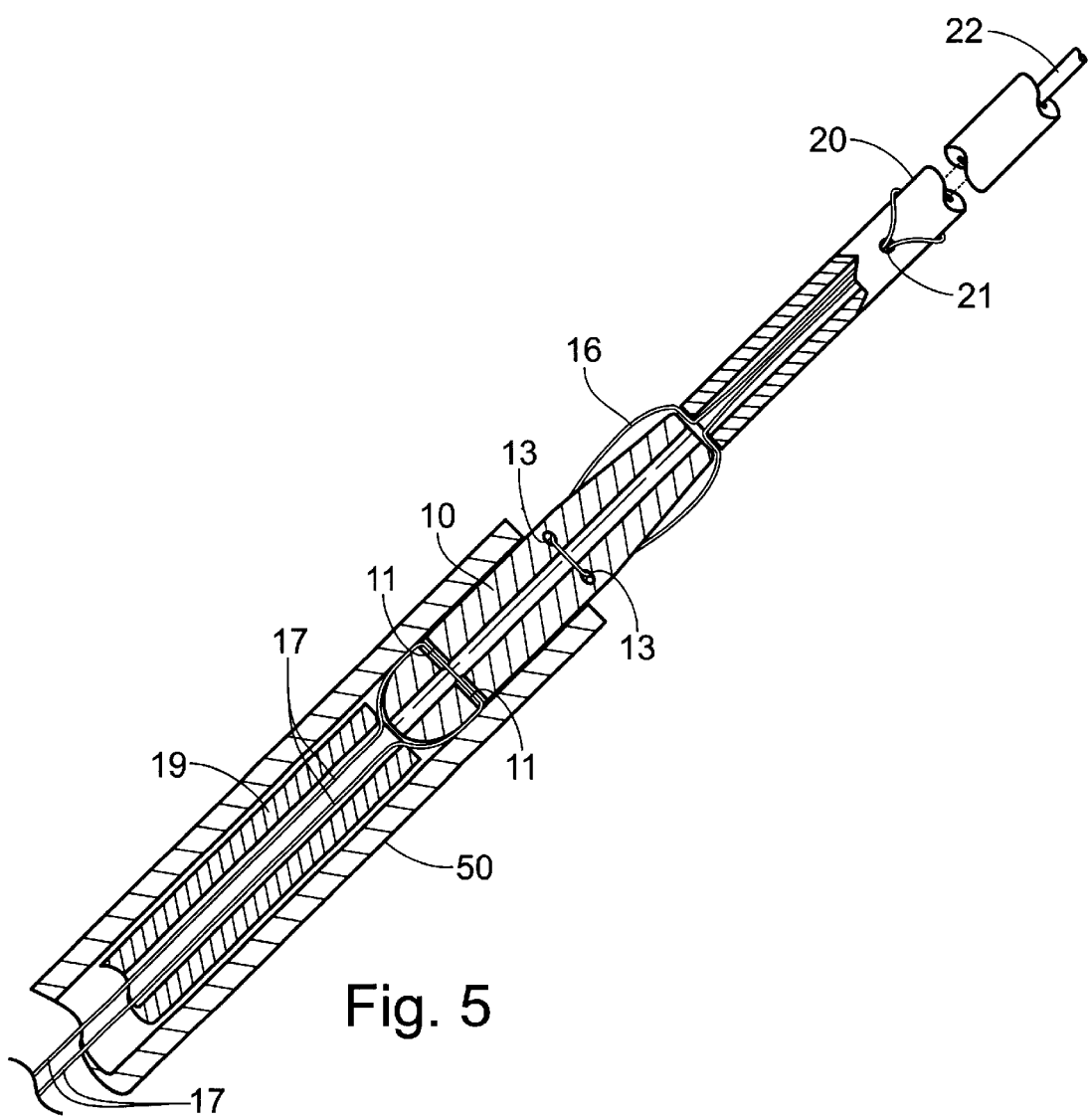

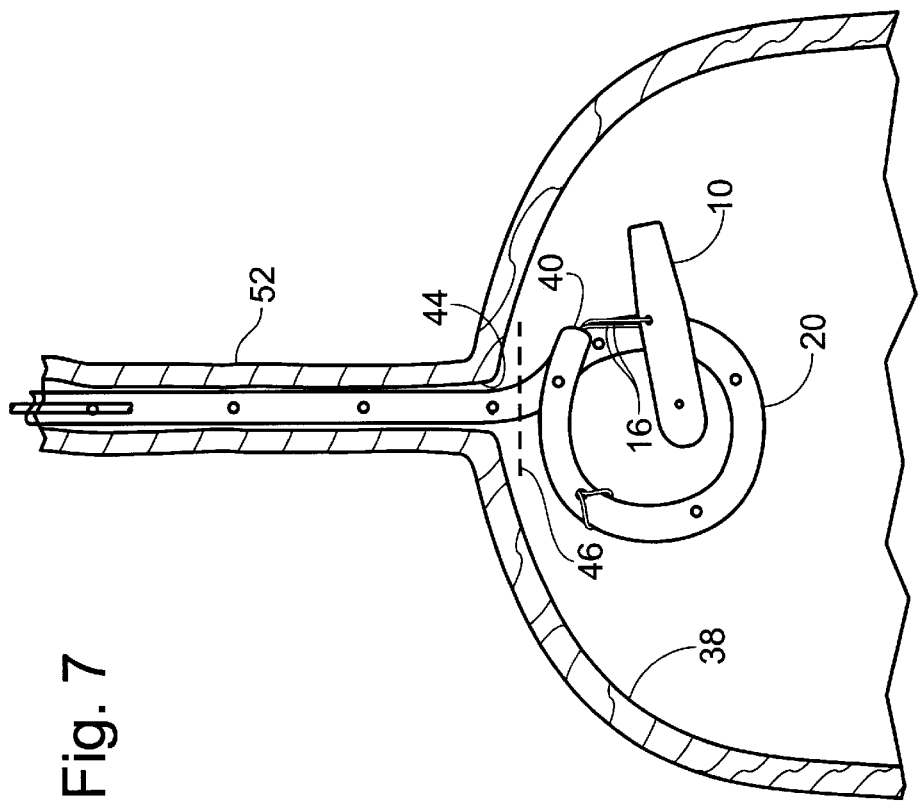
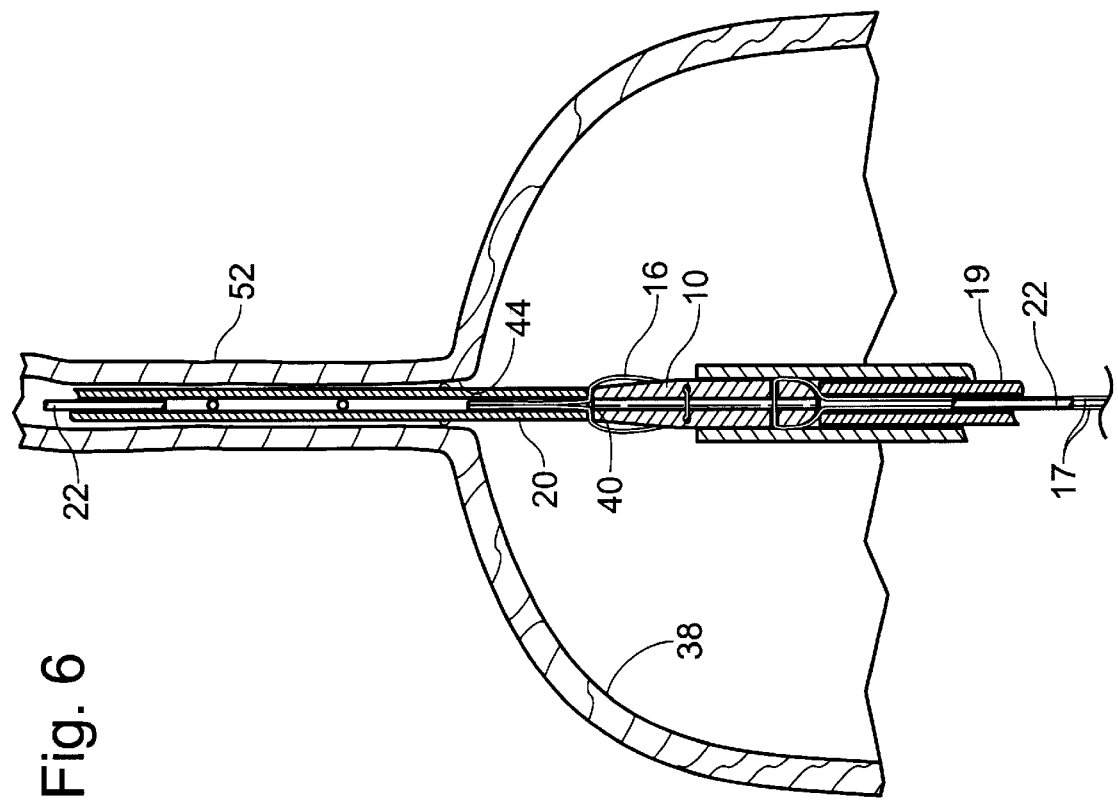

STENT PLACEMENT AND REMOVAL

This application is a continuation of Ser. No. 09/074,991, filed on May 8, 1998, now U.S. Pat. No. 6,258,098.

TECHNICAL FIELD

This invention relates to placement and removal of full-length or shortened ureteral stents, or stents in other hollow or tubular structures, which stents may be removed by means of a magnet.

BACKGROUND OF THE INVENTION

Ureteral stents are used to provide drainage of urine from the kidneys to the bladder. The stent is a flexible, tubular structure that is constructed of relatively inert material. The stent is perforated to have a plurality of small drainage holes along its length. Some stents are shaped to define "hooks" at either end. The hooks prevent migration of the tube from the kidney toward the bladder or from the bladder upwards.

Normally, indwelling stents must be periodically removed or replaced. Conventional stent removal procedures are complex and may be painful, sometimes requiring general anesthesia.

The presence of a stent within the lower ureter and within the bladder may cause considerable irritation to some patients. To alleviate this irritation, stents can be shortened. The stent is shortened at the distal (bladder) end. Thus, the distal end of the shortened stent resides in the ureter, remote from the bladder and the ureteral orifice. The ureteral orifice is the junction of the ureter and the bladder. A thin thread may be attached to the shortened stent to extend into the bladder and provide a means for later removing the stent. To remove the shortened stent, the thread must be endoscopically visualized, grasped, and withdrawn. Although this is a relatively simple procedure, it requires specialized instruments used by an urologist in a sterile setting. Here, too, general anesthesia is sometimes required.

Procedures for non-surgical removal of magnetically-attractible objects from a body cavity or tube have been used in the past. For example, U.S. Pat. No. 4,790,809 to Kuntz discloses a specially configured stent that carries a magnetically attractive tip. The tip is fastened to the hooked, distal end of the stent, which end resides in the bladder.

To remove the Kuntz stent, a catheter having a magnetized end is introduced into the bladder to attract and connect to the special tip of the stent. Apparently, the tip of the Kuntz stent may be caught by the magnet-tipped catheter in a manner that permits complete removal of the stent upon withdrawal of the catheter. Otherwise, Kuntz notes that the catheter and stent combination may be withdrawn just enough for the hooked end of the stent to be reached with a forceps or other grasping device, then completely removed. Apparently, Kuntz does not contemplate shortened-stent placement and removal.

SUMMARY OF THE INVENTION

The present system provides a stent assembly, system, and method for placement of ureteral stents, and for non-surgical removal of the stent assembly.

As one aspect of the invention, a conventional stent is modified to have connected to it a ferromagnetic member. The ferromagnetic member is biocompatible and is in the form of an elongated bead and is connected to the distal end of the stent by a tether. This permits the ferromagnetic member to be disposed in the bladder, suspended from the stent while the stent is positioned in the ureter. The bead is inserted at the time of insertion of the stent via a standard cystoscope that includes a guide wire and pusher.

The stent may be shortened to a length of choice prior to insertion, or left full-length. The shortened stent and tethered bead are inserted as a unit. The bead is shaped to temporarily penetrate the ureter as the bead is pushed with the shortened stent into the ureter to the desired position of the stent. The bead is provided with a mechanism that permits only the bead to be withdrawn from the ureter, pulled back into the bladder under visual control, once the shortened stent is properly positioned.

If a full-length stent is used, the bead does not, even temporarily, penetrate the ureter.

The stent assembly is readily removed by a non-surgical procedure that involves blind insertion of a magnet-tipped catheter into the bladder. The magnet engages the ferromagnetic bead, and the overall stent/tether/bead assembly is easily removed as the catheter is withdrawn.

As another aspect of this invention, the tether is flaccid, thereby permitting the suspended bead to move relative to the indwelling stent. This arrangement minimizes patient irritation that might otherwise occur if the tether were somewhat rigid or resilient.

DESCRIPTION OF THE DRAWINGS

FIG. 4 is a view, partly in section, of a magnet-tipped catheter component of the system.

FIG. 5 shows the primary components of the system, which can be advanced, as a unit, into position within the patient via a conventional cystoscope, guide wire, and pusher.

FIG. 6 illustrates the advancement of a full-length stent, tether, and bead assembly, relative to the ureteral orifice, as the stent is moved onto position.

FIG. 7 illustrates a full-length stent positioned in the ureter with the insertion instruments removed and the tethered bead suspended in the bladder.

DESCRIPTION OF A PREFERRED EMBODIMENT

Figure 1:
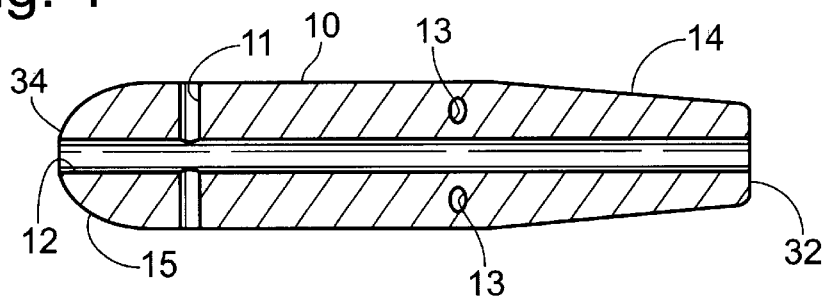
FIG. 1 is a sectional view of the bead component of a preferred embodiment of the stent placement and removal system of the present invention.
Figure 2:
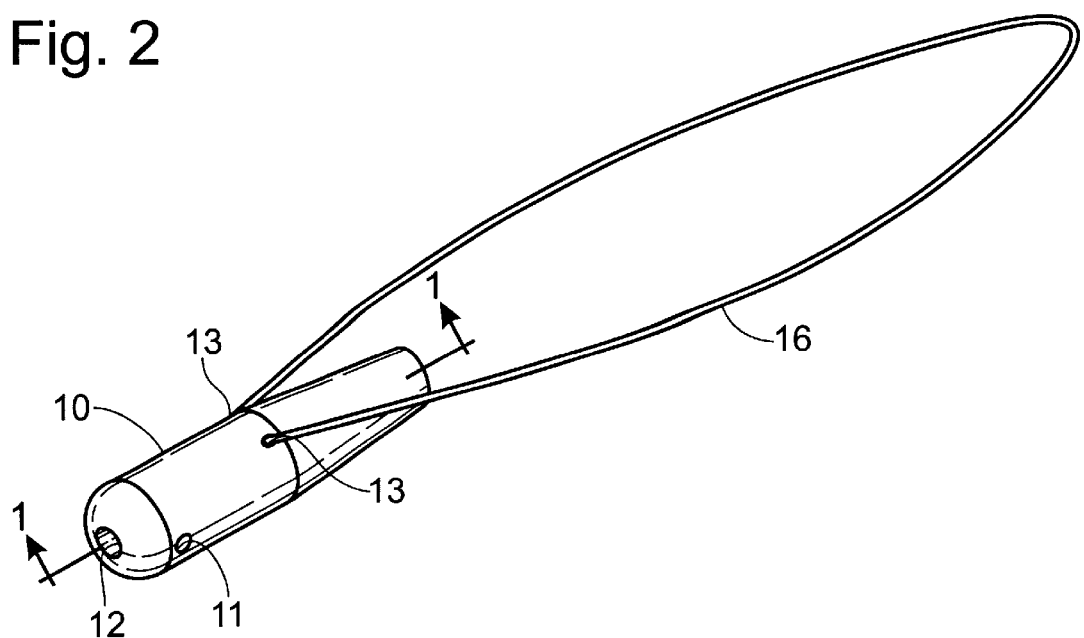
FIG. 2 is a pictorial view of the bead with a tether provided on the proximal end of the bead.

The preferred embodiment of the bead component 10 of the present invention is shown enlarged in FIG. 1. FIG. 2 depicts the bead 10 and connected tether 16. As will be explained, the tethered bead is connected to the distal end of a conventional stent (full-length, or shortened) for the purpose of converting that stent into one that may be non-surgically removed using a magnet-tipped catheter.

The bead 10 is, primarily, a ferromagnetic member. In this regard, the term "ferromagnetic" is meant to include the characteristic of substances comprised of iron, nickel, or cobalt and various alloys that are attracted to a magnet. Preferably, the bead 10 is stainless steel and may be coated with a smooth layer of, for example, polytetrafluoroethylene, which can be characterized as "biocompatible" in that it prevents reaction of the bead 10 with urine. It is contemplated that the bead 10 may be a magnet.

In the present embodiment, the bead is an elongated member, between 6 mm and 12 mm in length. The preferred shape of the bead 10 features a large-radius, proximal end taper 14. That is, about one-third of the length of the bead tapers from the full outside diameter of the bead (between 2.25 and 4.5 mm) to a minimum outside diameter of about 1.8 mm at the proximal end 32 of the bead. The outside diameter of the proximal end 32 of the bead generally matches that of the distal end of the stent 20 (FIG. 5).

The distal end 34 of the bead 10 has a smaller-radius taper 15. As will become clear, the tapered shape of both ends of the bead facilitates movement of the bead through a cystoscope, and, in the case of a shortened stent, into and out of the ureter.

As best shown in FIGS. 1 and 5, the bead 10 includes a central (i.e., through its long axis) guide lumen 12. The guide lumen 12 allows a commonly used guide wire 22 to be passed through the bead, thereby enabling the bead to be later advanced up the guide wire 22 as the stent and bead 10 are positioned within the patient, typically under fluoroscopic control.

As noted, the bead 10 is connected to the stent 20 by the tether 16. To this end, the bead 10 has, located near its midpoint, a pair of small-diameter openings 13. The openings 13 are spaced apart and extend through the bead in a direction generally perpendicular to the long axis of the bead. Alternatively the openings may be angulated and diverging in the direction toward the proximal end 32 of the bead. The tether 16 is threaded through both openings 13 to connect the tether to the bead 10. Alternatively, each free end of the tether is fixed, such as by crimping, to one of the openings. The tether portion of the tether that extends from the bead defines an endless loop that is connectable to the conventional, perforated stent, as described below.

It is contemplated that a single transverse opening 13 in the bead would suffice for connecting the tether and bead. The tether would be passed through the single opening before being formed into the endless loop.

Referring, momentarily, to FIG. 7, that figure shows a full-length stent positioned within a ureter 52. The distal end 40 of the stent has attached to it a tether 16 that connects the stent to the bead 10 which is disposed in the bladder 38. In this embodiment, the stent 20 extends through the ureteral orifice 44.

The tether 16 is made of a nylon or other biocompatible, thin, flexible, high-break-force line. The tether is flaccid in the sense that it lacks any significant resilience, and it readily yields to all but tensile force. As a result, the bead—once disposed in the bladder 38—is suspended from the distal end 40 of a stent and is not forced or urged against the wall of the bladder 38. This suspension of the bead, therefore, minimizes irritation of the bladder, which might otherwise be present if the bead were in some way urged into contact with the wall of the bladder.

Even though FIG. 7 illustrates an indwelling stent 20 having a hook-shaped distal end 40 (The hook is intended to halt migration of the stent toward the kidney.), it is contemplated that no such hooked end is required.

For instance, the stent 20 could be terminated with a straight end, such that the portion of the stent illustrated below the dashed line 46 in FIG. 7 would not be present. The bead 10, therefore, would be suspended by the tether from near that location 46 of the distal end of the stent. In this arrangement, the possibility of irritation attributable to a relatively large, hooked end of the stent would be eliminated.

Figure 10:
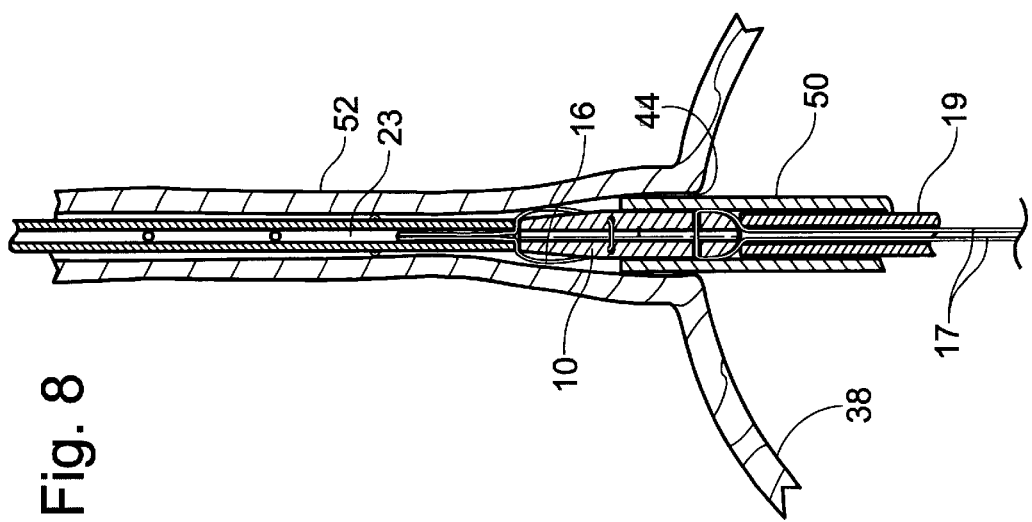
FIG. 10 illustrates a shortened stent positioned in the ureter with the insertion instruments removed and the tethered bead suspended in the bladder.

The bead 10 is generally free to rotate relative to the tether 16 to which it is connected. The tether is attached to the bead at a location generally aligned with the center of mass of the bead, but offset somewhat from the long axis of the bead. As a result, the bead tends to hang from the tether with its long axis oriented generally perpendicular to the length of the ureter, as shown in FIGS. 7 and 10, thereby preventing the suspended bead from migrating into the ureteral orifice. Also, and irrespective of the orientation of the bead, the suspended bead 10 is sized so that it will not migrate into the ureter in the absence of a pushing force with the bead properly aligned with the ureter. Moreover, if the tether is made short enough, the bead thus prevents upward (toward the kidney) migration of the stent.

In instances where a shortened stent 23 is employed (that is, a stent having a distal end 42 that resides in the ureter 52, away from the ureteral orifice 44—see FIG. 10), the thin, flaccid tether 16 extends between the distal end 42 of the shortened stent 23, through the ureteral orifice 44, to the bead 10 that is within the bladder 38. Thus, the very thin, flaccid tether prevents irritation that would occur as a result of the presence of an indwelling stent passing through the ureteral orifice.

Returning to FIGS. 1, 2, and 5, the bead 10 is also provided with a larger diameter passage 11 which allows a flexible line 17 to be threaded through the bead. Such a line 17 would be employed for withdrawing the bead from the ureter to locate the bead in the bladder after a shortened stent is in position. This is explained more below.

As noted above, the system of the present invention may be used with any conventional ureteral stent, such as those designated "Bander Ureteral Diversion Stents" and manufactured by Cook Urological Incorporated, of Spencer, Ind. Such stents are flexible, tubular members that, in addition to a central lumen, include spaced apart perforations 21 (FIG. 5) that serve as drain holes. Described next is an elegantly simple technique for attaching the looped tether to a selected portion on the distal end of the stent.

Figure 3:
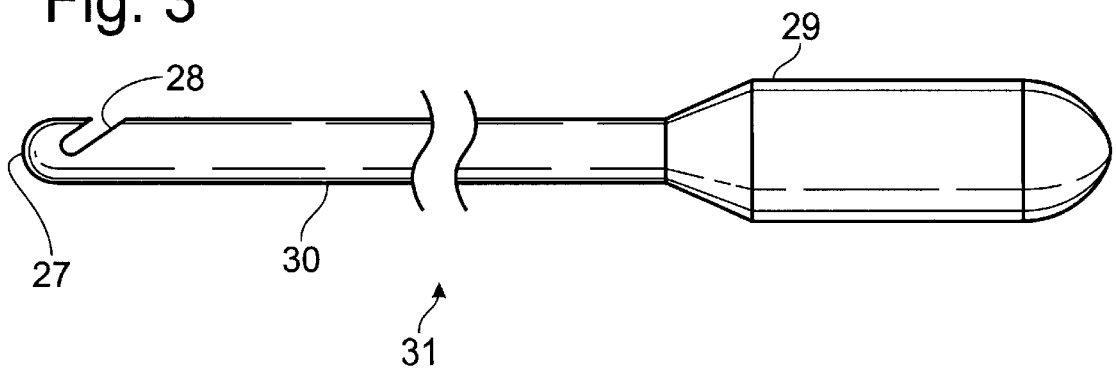
FIG. 3 is an enlarged side view of a needle that is useful for connecting the tether to a conventional ureteral stent.

FIG. 3 shows an elongated instrument or needle 31 for attaching the tether 16 and stent 20. The needle 31 is pointed but not sharp at its proximal end 27. The needle 31 also has a slot 28 near its proximal end, thus defining a hook at that end of the needle. The distal end of the needle is fastened to a handle 29.

The needle is sized to pass its hooked end through a perforation 21 from outside the stent to inside of the central lumen of the stent, without damaging the stent. The end 27 of the needle is then protruded from the distal end of the stent. The tether 16 is moved into the slot 28, and the needle, while engaging the tether is retracted through the lumen and perforation so that a portion of the tether loop is exposed outside of the stent, emerging from the perforation. The proximal end of the stent is moved through this loop portion, which will now provide an assured connection of the bead 10 and tether 16 to a stent, as best seen in FIG. 5.

FIG. 5 shows an assemblage including a guide wire 22, a hollow pusher 19, the bead 10, and the stent 20 all being advanced as a unit through and from a cystoscope 50. FIG.

5 also shows a positioning line 17 threaded through the passage 11 in the bead 10 and then through the inner lumen of the pusher 19. This positioning line 17 extends from the bead to the outside of the cystoscope, exposed for grasping by the user. The bead 10 is fastened to the stent 20 by the tether 16, which, as described above, has been threaded through the central lumen of the stent 20 and through the perforation 21 of the stent 20 then looped around the stent 20 at the level of the selected perforation 21 of the stent 20.

FIG. 6 shows the initial stage of inserting a full-length stent 20 which has a bead 10 connected to its distal end. This stage positions the distal end of the stent 20 in the bladder 38 with the bead 10 well away from the ureteral orifice 44. Once the distal end of the stent 20 is in the bladder and the proximal end of the stent is in the kidney (not shown), the guide wire 22 and pusher 19 are removed. This allows the stent 20 to assume its hooked-end position, said to help prevent migration of the stent into the ureter (FIG. 7). As noted, in this position, the bead 10 is suspended from the stent 20 by the tether 16.

Although FIG. 5 shows the assembly with positioning line 17 in place, it will be appreciated that for the placement of full-length stents (FIGS. 6 and 7) there is no need for the line, and it may be omitted.

Figure 8:
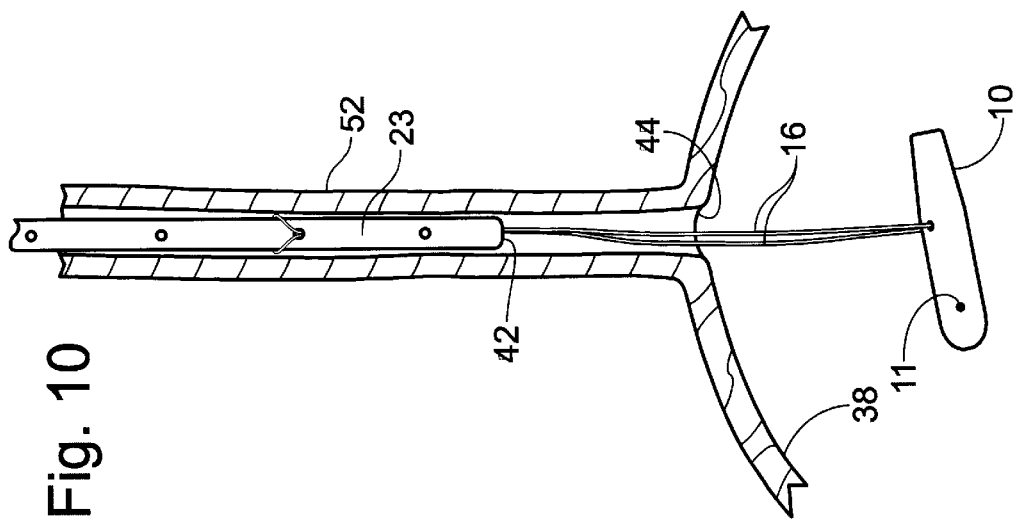
FIG. 8 illustrates the advancement of a shortened stent, tether, and bead assembly, relative to the ureteral orifice, as the stent is moved onto position.
Figure 9:
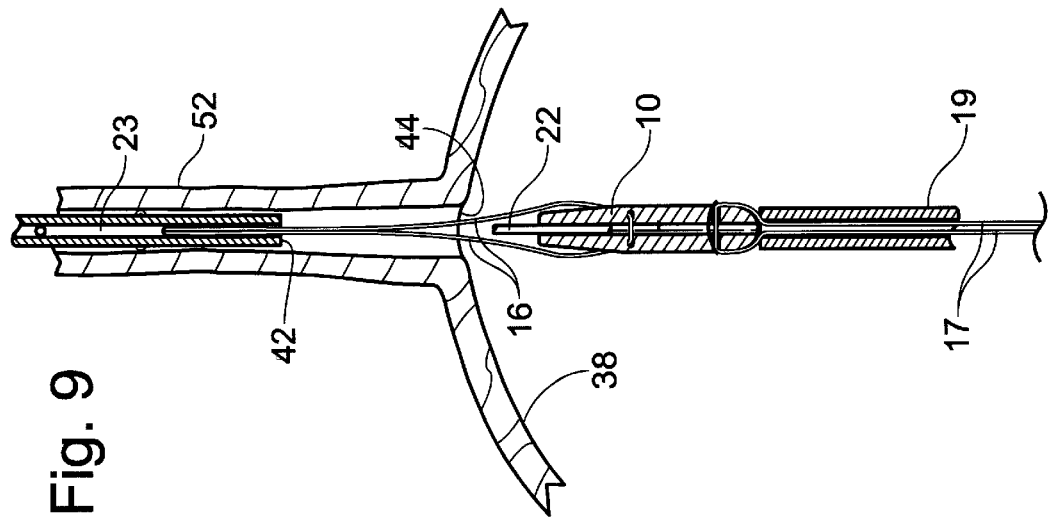
FIG. 9 illustrates the step of withdrawing the bead from the ureter once the shortened stent is pushed into proper position.

FIGS. 8, 9, and 10 show three stages of the insertion of a shortened stent 23. The distal end 42 of such a stent is ultimately positioned in the ureter 52. To accomplish this positioning, the bead 10 and the proximal end of the pusher 19 are pushed into the ureter 52 as shown in FIG. 8. That is, the bead 10 completely or partially penetrates (proximal-end first) the ureter 52. The guide wire 22 is then withdrawn.

The second stage of the positioning of the shortened-stent system, shown in FIG. 9, comprises the removal of the pusher 19, followed by the bead 10. Preferably, the bead is removed by pulling on the positioning line 17 (that is, the outer ends of the line that are exposed to the user) after, or simultaneously with removing the pusher 19. This withdraws the bead from the ureter, distal-end first. In this regard, the tether 16 is of a length such that there is sufficient slack to allow the withdrawal of the bead from the ureter to the bladder without pulling the stent 23 toward the bladder. Once the bead is withdrawn, the line 17 is removed from (slid through) the bead, leaving the bead 10 suspended by the tether 16 spaced from the ureteral orifice 44 and disposed within the bladder 38.

Preferably, the passage 11 through which the positioning line 17 passes is located near the distal end and passes diametrically through (or close to diametrically through) that end of the bead. This arrangement is best to ensure that the bead is withdrawn from the ureter along a straight path to avoid damage to the wall of the ureter.

FIG. 4 depicts is a component of the system that enables non-surgical removal (that is, no endoscopy is required) of both a full-length and shortened stent. The component, designated a retrieval catheter 24 comprises a conventional Foley catheter that is modified to serve as the retrieval catheter 24. Specifically, the catheter includes a magnet 26 mounted at its proximal tip. The magnet 26 is part of an assembly which consists of a grooved end 25 that is inserted into the catheter and acts as a barb to retain the magnet affixed to the catheter 24. The magnetic material of the retrieval magnet 26 may be covered with a biocompatible inert layer 30.

The magnet-tipped end of the retrieval catheter is inserted, through the urethra and into the bladder, whence it magnetically engages the suspended ferromagnetic bead 10.

Then, the withdrawal of the catheter 24 brings with it the bead and tether-connected stent. Preferably, the magnet 26 is rounded to avoid injury to the patient.

As the magnet 26 approaches the bead 10, the magnetic flux acting on the bead 10 should cause the bead to rotate relative to the tether from its normal, suspended position, so that one of the ends of the bead swings about 90 degrees into contact with the magnet 26. As a result, the bead will be oriented generally coaxially with the end of the retrieval catheter 24 that carries the magnet 26. If this orientation is not attained in the bladder, as the retrieval catheter magnet and bead enter the urethra passage, the urethra will assure the axial alignment of the assembly. This orientation is desired for sure and comfortable removal of the bead through the urethra. It will be appreciated that this rotation of the bead will be assured where the bead is magnetized, and one of its ends has a polarity opposite that of the catheter magnet 26.

While the present invention has been described in terms of a preferred embodiment, it will be appreciated by one of ordinary skill that the spirit and scope of the invention is not limited to those embodiments. For example, the stent system may be universal in the sense that it may be employed in other cavities, etc. of the human anatomy.

Also, the indwelling bead could be made as a magnet, with the retrieval catheter tipped with ferromagnetic material. Although a rare-earth magnet is preferred, other types, including electromagnets could be employed with the retrieval catheter. In addition, the bead may be of a more ball shape rather than the described elongated bead.

Thus the invention is considered to extend to the various modifications and equivalents as defined in the appended claims.

What is claimed is:

1. A stent assembly, comprising:
  a stent having a distal end;
  a ferromagnetic member wherein the ferromagnetic member is an elongated member and includes a lumen extending axially therethrough; and
  a flaccid tether that readily yields to all but tensile force, the tether connecting the ferromagnetic member to the distal end of the stent.

2. A stent placement and removal assembly, comprising:
  a stent having a distal end;
  a ferromagnetic member wherein the ferromagnetic member is an elongated member and includes a lumen extending axially therethrough;
  a flaccid tether that readily yields to all but tensile force, the tether connecting the ferromagnetic member to the distal end of the stent; and
  a catheter having magnet means mounted thereto for magnetically attracting the ferromagnetic member when the magnet means is brought into proximity with the ferromagnetic member.

3. A method of converting a perforated ureteral stent into one that may be removed from a patient's ureter by use of a magnet, the method comprising the step of attaching to one end of the stent an elongated, flaccid tether to which tether is connected a ferromagnetic member at a location spaced from the end of the stent and movable relative to the stent, thereby enabling insertion of the stent in the patient's ureter, the ferromagnetic member disposed within the patient's bladder and accessible to a magnet while the stent is in the ureter.

4. A kit for converting a ureteral stent into one that may be removed from a patient's ureter by use of a magnet, wherein the stent has a central lumen and at least one perforation, the kit comprising:

a ferromagnetic member including a passage formed through the ferromagnetic member at one end thereof to facilitate attachment of a line to the ferromagnetic member; and a tether connected to the ferromagnetic member, the tether including a loop that extends from the ferromagnetic member, thereby to enable the ferromagnetic member to be attached to a stent by the tether while the ferromagnetic member is remote from the stent; and an elongated instrument having one end movable relative to the ferromagnetic member, that end being sized to extend through both the lumen and perforation of the stent and engage the tether for connecting the tether to the stent.

5. A method of inserting a ureteral stent, comprising the steps of:

locating the stent within a patient's ureter by guiding through a cystoscope a unit that includes a ferromagnetic member, the stent, a guide wire, and a pusher member; and suspending from the stent the ferromagnetic member to be disposed in the bladder of the patient after temporarily penetrating the ureter with the ferromagnetic member.

6. An assembly for facilitating placement and removal of a stent, comprising:

a ferromagnetic member having a generally circular cross section and wherein a transverse passage extends diametrically through the ferromagnetic member;

a tether connected thereto, the tether extending from the ferromagnetic member thereby to enable the ferromagnetic member to be attached to a stent by the tether while the ferromagnetic member is remote from the stent; and a magnet member for magnetically attracting the ferromagnetic member when the magnet member is brought into proximity with the ferromagnetic member.

7. The assembly of claim 6 wherein the tether is flaccid, thereby enabling the ferromagnetic member to be suspended from the tether and move freely relative to any stent to which the tether may be attached.

8. The assembly of claim 6 wherein the tether extends through the passage to connect the ferromagnetic member to the tether.

9. The assembly of claim 8 wherein the ferromagnetic member is an elongated member and wherein the passage extends in a direction that is generally perpendicular to a long axis of the member, the ferromagnetic member being rotatable relative to a portion of the tether that extends through the passage.

10. The assembly of claim 6 wherein the ferromagnetic member has opposing ends that are tapered to facilitate penetration into and withdrawal from a ureter.

11. An assembly for facilitating placement and removal of a stent, comprising:

a ferromagnetic member, the ferromagnetic member being an elongated member that includes a lumen extending axially therethrough;

a tether connected thereto, the tether extending from the ferromagnetic member thereby to enable the ferromagnetic member to be attached to a stent by the tether while the ferromagnetic member is remote from the stent; and a magnet member for magnetically attracting the ferromagnetic member when the magnet member is brought into proximity with the ferromagnetic member.

12. The assembly of claim 11 wherein the ferromagnetic member has a long axis and wherein the tether is connected at a location on the ferromagnetic member such that the ferromagnetic member is suspended by the tether with the long axis of the ferromagnetic member generally perpendicular to the length of the tether.

13. A method of positioning a ureteral stent, comprising the steps of:

locating the stent within a patient's ureter;

suspending from the stent by a flaccid tether a ferromagnetic member so that the ferromagnetic member is disposed in the bladder of the patient.

* * * * *